United States Patent
Raisaro et al.

(10) Patent No.: US 9,524,370 B2
(45) Date of Patent: Dec. 20, 2016

(54) METHOD FOR PRIVACY-PRESERVING MEDICAL RISK TEST

(71) Applicant: Ecole Polytechnique Federale de Lausanne (EPFL), Lausanne (CH)

(72) Inventors: Jean L. Raisaro, Lausanne (CH); Erman Ayday, Renens (CH); Paul McLaren, Lausanne (CH); Jean-Pierre Hubaux, St-Sulpice (CH); Amalio Telenti, La Jollla, CA (US)

(73) Assignee: Ecole Polytechnique Federale de Lausanne (EPFL) (CH)

( * ) Notice: Subject to any disclaimer, the term of this patent is extended or adjusted under 35 U.S.C. 154(b) by 0 days.

(21) Appl. No.: 14/531,034

(22) Filed: Nov. 3, 2014

(65) Prior Publication Data

US 2016/0125141 A1    May 5, 2016

(51) Int. Cl.
| | | |
|---|---|---|
| *G06F 21/00* | (2013.01) | |
| *G06F 19/00* | (2011.01) | |
| *H04L 9/00* | (2006.01) | |
| *H04L 9/08* | (2006.01) | |
| *G06F 21/62* | (2013.01) | |
| *G06F 19/22* | (2011.01) | |
| *G06F 19/28* | (2011.01) | |

(52) U.S. Cl.
CPC .............. *G06F 19/322* (2013.01); *G06F 19/22* (2013.01); *G06F 19/28* (2013.01); *G06F 21/6245* (2013.01); *H04L 9/008* (2013.01); *H04L 9/0861* (2013.01)

(58) Field of Classification Search
CPC combination set(s) only.
See application file for complete search history.

(56) References Cited

U.S. PATENT DOCUMENTS

| | | | | |
|---|---|---|---|---|
| 8,316,237 | B1 * | 11/2012 | Felsher ................. | H04L 9/0825 380/282 |
| 2014/0075183 | A1 * | 3/2014 | Wang ..................... | G06F 19/22 713/150 |
| 2015/0154406 | A1 * | 6/2015 | Naehrig ................. | G06F 19/28 713/165 |

FOREIGN PATENT DOCUMENTS

EP    2709028 A1    3/2014

OTHER PUBLICATIONS

Fons Bruekers et al., "Privacy-Preserving Matching of DNA Profiles," May 2008, 16 pages.
Murat Kantarcioglu et al., "A Cryptographic Approach to Securely Share and Query Genomic Sequences," IEEE Transactions, vol. 12, No. 5, Sep. 2008, pp. 606-617.

* cited by examiner

Primary Examiner — Ghazal Shehni
(74) Attorney, Agent, or Firm — Blank Rome LLP (57) ABSTRACT

A privacy-preserving method for performing a disease susceptibility test on a patient, said method comprising:
  (I) performing homomorphic computations,
  (J) obtaining a test result which is partly decrypted with a first part (prk1 resp. prk2) of a private key,
  (L) decrypting said partly decrypted result with a second part (prk2 resp. prk1) of said private key,
  wherein said homomorphic computations are based on encrypted genomic markers of the patient, on encrypted clinical and/or environmental markers, and on encrypted ancestry markers of the patient.
The invention is also related to a method for inferring ancestry in the encrypted domain.

20 Claims, 6 Drawing Sheets

| | SNV$_1$ | SNV$_2$ | ... | SNV$_M$ |
|---|---|---|---|---|
| P$_1$ | (0) | (1) | | (0) |
| P$_2$ | (1) | (1) | | (0) |
| P$_3$ | (2) | (2) | | (0) |
| ... | | | | |
| P$_N$ | (0) | (1) | | (1) |

400

| | Phen$_1$ | ... | Phen$_N$ |
|---|---|---|---|
| | (1) | | (1) |
| | (0) | | (0) |
| | (0) | | (0) |
| | (1) | | (0) |

401

| | Anc$_1$ | Anc$_2$ | Anc$_3$ |
|---|---|---|---|
| | (1) | (0) | (0) |
| | (0) | (1) | (0) |
| | (0) | (0) | (1) |
| | (1) | (0) | (0) |

METHOD FOR PRIVACY-PRESERVING MEDICAL RISK TEST

FIELD OF THE INVENTION

The present invention relates to personalized medicine. More specifically, the present invention concerns a privacy-preserving method for performing disease susceptibility tests on a patient.

DESCRIPTION OF RELATED ART

The evolution of sequencing technologies has generated a significant growth in genomics as a research discipline with many application possibilities. This genomic information is often used to infer the susceptibility of a patient to some diseases and to optimize treatments.

With upcoming developments, DNA tests may soon become a commodity offered at various locations such as pharmacies, stores, or at home. This extensive usage of genomic data poses important privacy concerns: (i) genetic diseases and propensity can be unveiled; (ii) potentially sensitive information can be leaked, such as ancestry and paternity; (iii) information on family members can be imputed from the genome of a given individual; and (iv) genomic data is a personal unique identifier.

Hence, it is a common belief that genomic information should be handled (i.e., stored, managed and processed) with care. Anonymization techniques are not sufficient since the genomic data is by itself identifying; therefore, re-identification of anonymized data is often possible for example when the genomic data of known related parents is available.

Recently, researchers from both the computer science and medical fields have started collaborating to design new cryptographic solutions that protect individuals' genomic privacy. For example, F. Bruekers et al describe in "Privacy-Preserving Matching of DNA profiles", Tech. Rep., 2008, a privacy-enhanced comparison of DNA profiles for identity, paternity and ancestry tests using homomorphic encryption. This method is not related to risk evaluation.

EP2709028, whose content is hereby incorporated by reference, describes privacy-enhancing technologies for medical tests using genomic data. However, many diseases depend on different factors, and not only on genetic factors.

In <<A Cryptographic Approach to Securely Share and Query Genomic Sequences>>, IEEE Transactions on Information Technology in biomedicine, IEEE Service Center, Los Alamitos, Calif., US, 5. September 2008, pages 606-617, M. Kantarcioglu et al. describe cryptographic method that enables organizations to support genomic data mining without disclosing the raw genomic sequences. To this end, organizations store encrypted genomic sequence records into a centralized repository where the administrator can perform queries such as frequency counts without decrypting the data. This document is not related to medical risk evaluation; it is only useful for queries of genomic data.

BRIEF SUMMARY OF THE INVENTION

It is therefore an aim of the present invention to provide a further privacy-preserving method for evaluating the susceptibility of patients to risks.

According to one aspect, this aim is achieved by means of a privacy-preserving method for performing a disease susceptibility test on a patient, comprising:

(I) performing homomorphic computations, so as to retrieve an encrypted test result;

(J) partly decrypting said test result with a first part (prk1 resp. prk2) of a private key, (L) decrypting said partly decrypted result with a second part (prk2 resp. prk1) of said private key, wherein said homomorphic computations are based on encrypted genomic markers of the patient, on encrypted clinical and/or environmental markers, and on encrypted ancestry markers of the patient.

This method has the advantage to infer a risk such as a disease susceptibility, based on genomic factors, but also on non genomic factors, such as clinical and/or environmental factors, and on ancestry factors.

It is known that different ancestry groups, for example some ethnic groups, have different pre-dispositions to some diseases, or react differently to some treatments. The method thus uses this additional information, as well as clinical and/or environmental data, to infer the risk.

The method is based among others on homomorphic encryption, i.e., a specific form of encryption that supports some computations in the encrypted domain.

At least some of the genomic and non-genomic markers could be individually encrypted by using an additively homomorphic scheme, such as for example a Paillier cryptosystem or a modified version of the Paillier cryptosystem.

An additively homomorphic scheme has the following properties:

i. The product of two ciphertexts is equal to the encryption of the sum of their corresponding plaintexts:

$$[X] \times [Y] = [X+Y]$$

ii. A ciphertext raised to a constant number is equal to the encryption of the multiplication between the plaintext and that constant:

$$[X]^c = [cX]$$

According to one aspect, the method is also based on proxy re-encryption. Proxy re-encryption allows third-parties to alter a ciphertext, so that it can be decrypted by another. In particular, assuming a private key x is randomly split in two shares $x_1$ and $x_2$, such that $x=x_1+x_2$, proxy re-encryption enables an encrypted message [X] to be partially decrypted to ciphertext $[\hat{X}]$ using $x_1$. Then, $[\hat{X}]$ can be decrypted using $x_2$ to obtain the original plaintext message X.

In one aspect, the method further comprises:

(A) generating a pair of encryption keys comprising said private key and one public key corresponding to said private key;

(B) dividing said private key in said first and second parts;

(C) making a first one of said parts available to one user (such as for example a medical center MC) of said results, and a second one of said parts available to a Data Center (such as a storage and processing unit);

(D) retrieving a set of patient markers including said genomic markers and said clinical and environmental markers;

(E) individually encrypting a plurality of said patient markers with said public key;

(F) making at least some of said encrypted patient markers available to said Data Center.

The patient markers are thus encrypted so that the Data Center has no access to those markers—even if the Data Center has a part of the private key.

The homomorphic computations may be performed by the user. In this case, the encrypted result may be transmitted to the Data Center, which performs said step (J) of partly decrypting the result with its part of the private key. The step (L) of decrypting said partly decrypted result may be performed by the user with the other part of the private key. In this scenario, the Data Center has no access to the test results and does not know which test is carried out.

Alternatively, the homomorphic computations may be performed by the Data Center. In this case, the step (J) of partly decrypting the result is performed by the Data Center. The partly decrypted result is sent to the user, which performs said step (L) of decrypting said partly decrypted result with the other part of the private key. This embodiment reduces the number of exchanges between the Data Center and the user; however, the Data Center may learn which test is performed for the patient (without accessing to the result of the test).

The method may comprise a step (G) during which the user transmits to the Data Center a selection of identifiers of patient markers, at least some of said patient markers being required for said homomorphic computation; and a step (H) of retrieving in said Data Center patient markers corresponding to said identifiers.

The computation is thus based on a subset of all patient markers. The Data Center does not need to retrieve the other markers.

The identifiers may be encrypted with a symmetric key known by said user and unknown by said Data Center, so as to prevent said Data Center from knowing which patient markers are used for the test. This might make it more difficult for the Data Center to determine which test is performed.

The selection of identifiers may comprise dummy identifiers for markers with no contribution to said result. This might make it even more difficult for the Data Center to determine how many patient markers, and which patient markers, are used for the test, hence which test is performed.

The encrypted ancestry markers used for the homomorphic computation may be inferred from the encrypted genomic markers of the patient.

According to an independent aspect, the invention is thus also related to a method that allows a user to determine the ancestry group of a patient without giving to this user access to the actual genomic data of the patient.

According to one aspect, a method for ancestry inference and risk evaluation based on this ancestry information comprises a secure two-party protocol that takes place between a user, such as a medical center, and a data center.

The determination of ancestry information might be executed only once for a given user, for example as a pre-processing step before performing said susceptibility test.

The determination of ancestry markers might be executed for each user for which genomic data are available.

Alternatively, the determination of ancestry markers might be executed on demand when the corresponding markers are requested for a test for a given user.

The determination of ancestry markers could be performed in the Data Center on the encrypted genetic markers.

The determination of ancestry markers could be performed by a certified institution (CI) on the plaintext genetic markers before encryption.

Inferring the ancestry markers may be based on a principal component analysis (PCA).

Inferring the ancestry markers may be performed on encrypted principal components.

The ancestry inference may use a selection of patient markers and associated weights associated with said principal components.

In one preferred embodiment, those encrypted ancestry markers are inferred in the encrypted domain, from said encrypted genomic markers. Therefore, the unit responsible for the computation has no access to the ancestry information of the patient. This ancestry information is used in the evaluation of disease susceptibility, but does not need to be explicitly revealed to the user or to the Data Center.

The method may further comprise transmitting to said data center weights ($W_L$), and using said weights and said encrypted genomic markers for inferring an encrypted ancestry group with a principal component analysis.

The step of inferring the ancestry group may comprise a determination of the similarity between said genomic markers and a plurality of clusters, each cluster corresponding to one ancestry group.

The determination of similarity may be performed in the encrypted domain, in order to hide the result to the unit that determines this similarity.

The method may further comprise a step of performing a Principal Component Analysis on an external reference panel of plaintext genotypes, and a step of clustering the results of said Principal Component Analysis.

According to one aspect, the invention is also related to a data center comprising:

a storage module for storing a set of patient markers including genomic markers, clinical and environmental markers, and ancestry markers;

means for transmitting a selection of patient markers to a user (MC);

means for receiving an encrypted result from said user;

a cryptographic module arranged for decrypting said result with a part of a private key;

means for transmitting the partly decrypted result to said user.

Alternatively, in another embodiment, the invention is related to a Data Center comprising:

a storage module for storing a set of patient markers including genomic markers, clinical and environmental markers, and ancestry markers;

a computing module arranged for performing homomorphic computations based on said genomic markers, on said clinical and environmental markers, and on said ancestry markers, so as to retrieve an encrypted result;

a cryptographic module arranged for decrypting said result with a part of a private key;

means for transmitting the partly decrypted result to one user.

The computing module may be arranged for determining a similarity between some genomic markers and a plurality of clusters, so as to retrieve encrypted ancestry markers.

According to another aspect, the invention is related to a user system comprising:

means for transmitting to a Data Center encrypted identifiers of patient genomic, clinical and environmental, and ancestry markers;

means for receiving encrypted genomic, clinical and environmental, and ancestry markers;

computations based on said genomic markers, on said clinical and environmental markers, and on said ancestry markers, so as to retrieve an encrypted result;

means for transmitting the encrypted result to said Data Center;

means for receiving a partly decrypted result;

a cryptographic module arranged for decrypting said partly decrypted result with a part of a private key.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS OF THE INVENTION

Figure 1:
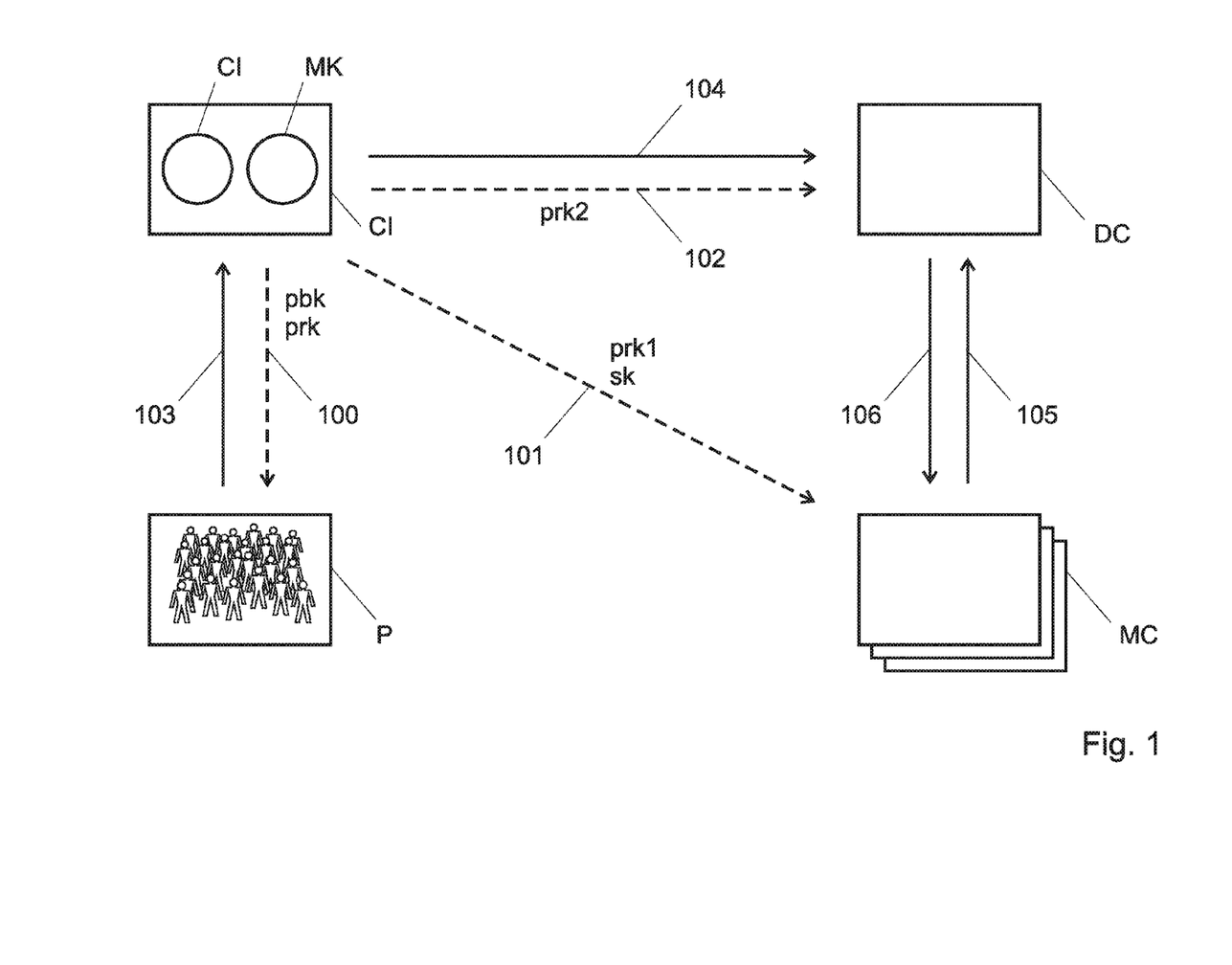
FIG. 1 is a schematic view of the main components or entities of a system according to the invention.

The system model illustrated on FIG. 1 includes the following components:

(i) A patient (P) that provides his genomic and non-genomic information to a certified institution (CI).

(ii) A certified institution (CI), responsible for genotyping P's biological DNA sample and outputting genomic markers, such as for example single-nucleotide polymorphisms (SNPs) that capture known functional variants, and non-genomic markers;

(iii) a key manager (MK), that manages the cryptographic keys, preprocesses the genomic and non-genomic markers, and individually encrypts each markers;

(iv) a Data Center (DC), such as a storage and processing unit, that stores the encrypted genomic and non-genomic marker for each enrolled patient; and (v) a user of the test results, such as a medical center (MC) that is the end-user of the data and queries the Data Center for test results, such as pharmacogenetic risk tests.

The various components might include organizations and/or apparatuses or systems. For example, the user MC could be an organization, such as a medical unit, an apparatus or a system, such as a processing unit, a computer, server, medical smart card, computer system, etc, that requests medical tests. Similarly, the Data Center DC could be embodied as an organization or as a processing unit, computer, server, computer system, etc that performs computation and storage tasks.

The various elements or units in FIG. 1 could communicate through any type of data network, for example over the Internet, over a LAN, cellular network etc. At least some data could be exchanged over VPN (virtual private network) connections. Some data could be signed and or encrypted before transmission.

In one embodiment, the CI and the MK are merged into a single trusted entity, such as an organization. The key manager could comprise a processing unit, such as server or server system, for generating and managing symmetric and/or asymmetric keys and for encrypting and signing data.

According to one aspect of the invention, the user MC can perform tests, such as pharmacogenic tests, disease susceptibility tests and ancestry tests, on a patient, without allowing the user or the Data Center DC to retrieve the patient's genomic and non-genomic data—at least until those two entities don't collude. For example, an insider at the DC or at the MC (e.g., a disgruntled or careless employee) or a hacker who, for example, breaks into the system, won't be able to obtain private genomic and non-genomic information about patients.

Figure 2:
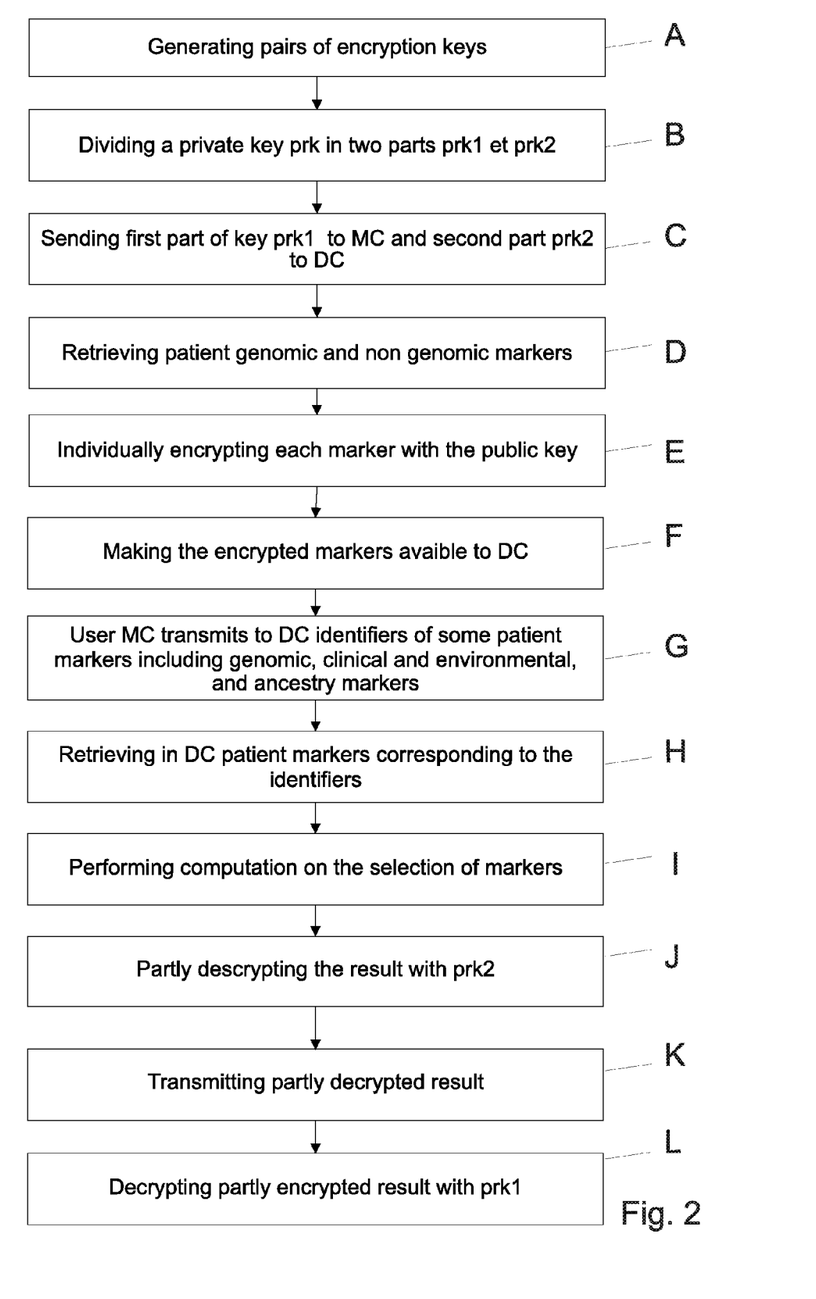
FIG. 2 is a simplified flowchart illustrating the main steps of a method according to the invention.

FIG. 2 illustrates the main steps of a method for inferring a patient ancestry group from genomic and non-genomic data. In step A, a pair of encryption keys comprising one public key pbk and one private key prk corresponding to this public key is generated, preferably by the key manager MK or under his supervision.

In step B, the private key prki for the i-th patient $P_i$ is divided in two parts $(prk_i^1, prk_i^2)$ of private keys. This division could be random and the two parts could have the same length, or a different length.

The key manager MK at the certified institution CI distributes to each patient $P_i$ the pair of cryptographic keys pbk, prk (arrow 100 on FIG. 1).

The key manager MK at the certified institution CI also establishes a first symmetric cryptographic key (or an asymmetric pair of keys) to protect the communication between the parties from eavesdroppers.

The key manager MK also establishes a second symmetric key SK which will be used to encrypt the markers identifiers toward the DC.

The CI, as a trusted entity, can also handle the update and the revocation of the cryptographic keys.

In step C, a first one of said parts $prk_i^1$ is made available to at least one user MC (arrow 101), and a second one of said parts $prk_i^2$ is made available to the Data Center DC (102). "To make available" includes for example to transmit, to distributed, to send, to save in a shared store, to send equivalent information, etc.

Thus no party (except the certified institution and the patient $P_i$) has the complete private key $prk_i$.

Note that for simplicity, we assume the presence of a single user MC. However, in the case of multiple MCs, the first part of the private key $prk_i^1$ is provided to each one of them.

In step D, a set of patient markers including genomic markers and non-genomic markers is retrieved, for example by the certified institution CI. The non-genomic markers include clinical and/or environmental markers. During this step, the patients $P_i$ enrolled in system provide, upon consent, to the CI their biological samples (e.g., saliva or blood), along with some non-genetic information (arrow 103). The CI genotypes the patient's $P_i$ biological samples and extracts PI's genetic markers, for example his personal set of SNPs, stored in row i of a table 200 illustrated on FIG. 3. It also stores non-genetic (phenotype) markers in row i of a table 201. Each column corresponds to one piece of phenotype information.

Please note that step D could be performed before, after or during any of the steps A to C.

Figure 3:
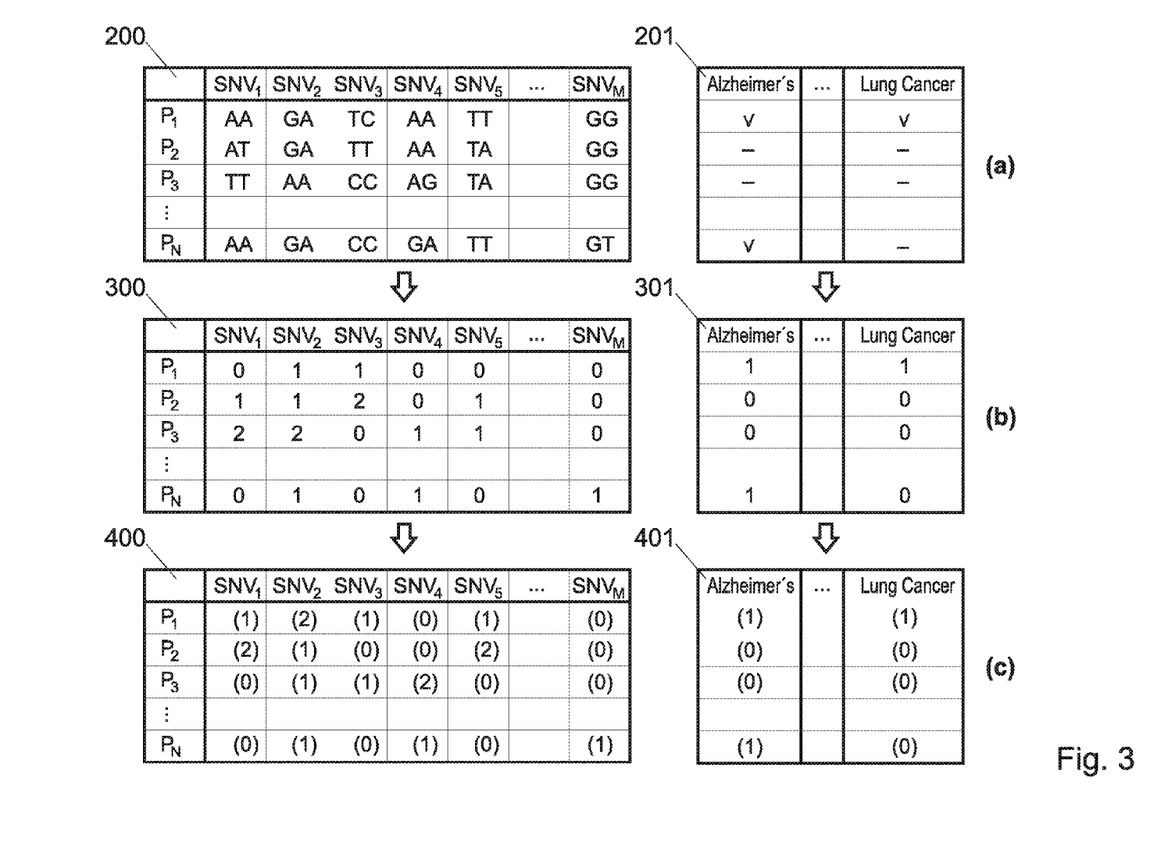
FIG. 3 illustrates examples of tables for storing raw, encoded and encrypted genomic and phenotype data for a plurality of patients.

In step E, some or all of said markers are individually encoded, resulting in encoded rows in tables 300, 301.

In general, a marker such as a SNP is encoded with the additive model. In such a model, each copy of an allele modifies the association with a given phenotype in an additive form. Let M denote the major allele and m the minor allele: Given its bi-allelic nature, a SNP can get value 0 when it is homozygous major (genotype MM), value 1 when it is heterozygous (genotypes Mm or mM), and value 2 when it is homozygous minor (genotype mm). Note that a dominant model or a recessive model could also be used within the method.

Some or all of those markers are individually encrypted with the patient's public key pbk, using for example Paillier system or a modified Paillier cryptosystem. The encryption could be performed by the certified institution CI or, preferably, by the key manager MK. Some markers could be pre-processed before encryption.

Figure 4:
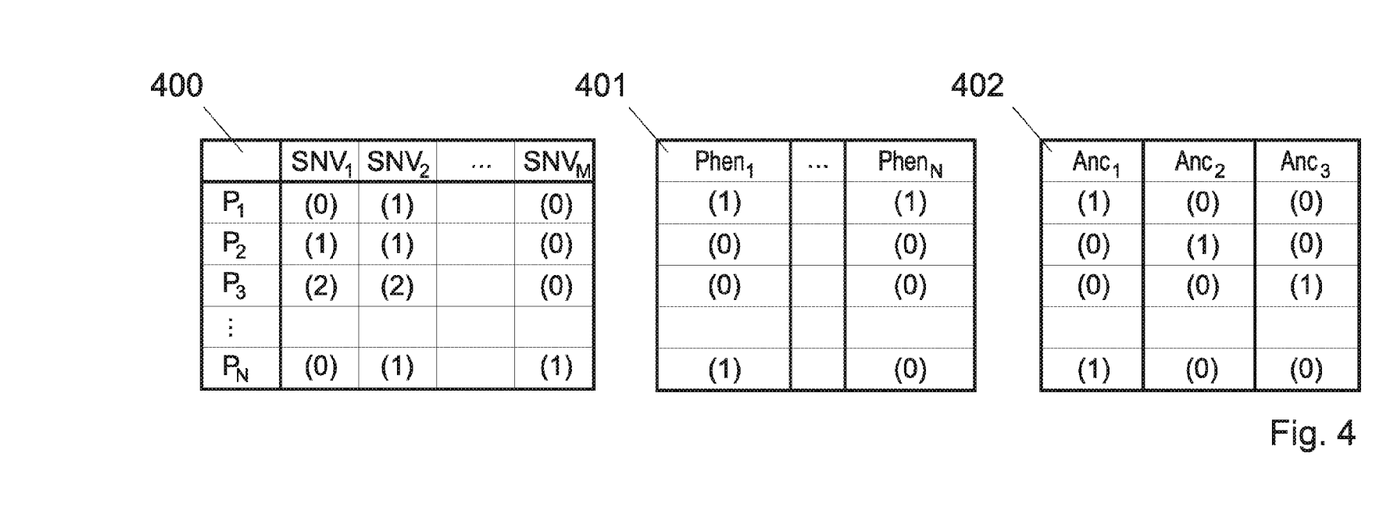
FIG. 4 illustrates examples of tables for storing encoded and encrypted genomic, phenotype and ancestry markers for a plurality of patients.

Let $pbk_i$ represent the public key for the i-th patient; then $[G_i^j]_{pbk_i}$ denotes the encrypted genotype of his j-th SNP and $[P_i^n]_{pbk_i}$ the encrypted status of his n-th non-genetic marker. For the sake of simplicity, in the rest of the application we refer to $[G_i^j]_{pbk_i}$ as $[G_i^j]$, and to $[P_i^n]_{pbk_i}$ as $[P_i^n]$, unless specified otherwise. Furthermore, we refer to [ $\mathbb{G}$ ] as the matrix 400 containing the encrypted and encoded SNPs and to [ $\mathbb{P}$ ] as the matrix 401 containing the encrypted and encoded non-genetic factors.

Eventually, the CI can encrypt from a few thousand to a few million SNP per individual. The number of encrypted non-genetic markers is much smaller and usually in the order of tens or hundreds.

Similarly, in the phenotype table $\mathbb{P}$, each row contains the encrypted phenotype markers of a single patient and each column specifies a phenotype's identifier. Each element $P_i^n$ of $\mathbb{P}$ denotes the n-th non-genetic marker for the i-th patient. The non-genetic markers include clinical and/or environmental status, such as a disease affection condition which can be encoded with a binary status. Hence, a non-genetic marker can be represented by a binary value where 0 represents the absence and 1 the presence of the affection. When the affection condition of a patient's non-genetic marker is unknown, the corresponding table element contains the "missing" tag. Phenotype tables containing non binary values, including discretized continuous values, could also be used.

Similarly to the encrypted genotype [ $\mathbb{G}$ ] and phenotype [ $\mathbb{P}$ ] tables 400, 401, the encrypted ancestry information for each patient (for example his ethnicity) can be represented in a table or matrix $\mathbb{A}$ (402), where each row contains the encrypted ancestry information for a single patient and each column specifies a single ancestry group (FIG. 4). Each element $A_i^k$ of the matrix contains a binary value (either 0 or 1) indicating in encrypted form whether the i-th patient belongs to the k-th ancestry group.

This encrypted ancestry information 402 be performed in the key manager MK by inferring the ancestry information for a patient, based on his unencrypted genomic markers, encoding this information, encrypting the corresponding ancestry markers with the user public key pbk, and sending the encrypted ancestry markers to the Data Center for storage and further use.

Preferably, the encrypted ancestry markers 402 corresponding to a patient are inferred in the encrypted domain, for example by the Data Center, using homomorphic computations based on the encrypted genomic markers. The result of this computation consists of the encrypted matrix [A] where each element of the i-th row is individually encrypted by the i-th participant's public key. We will describe later how this ancestry information could be retrieved from the encrypted genotype markers in table 400.

In step F, some or all of the encrypted markers $[G_i^j]$ and $[P_i^n]$ (as well as [ $\mathbb{A}_i^j$ ] if already available) are transmitted or otherwise made available to the data center DC where they are stored (arrow 104). Patient's data is anonymised, i.e. stored using pseudonyms (without revealing the identities of the patient) to prevent the Data Center DC from associating a marker to a specific individual patient. The use of pseudonyms thus precludes the association of a risk test to a patient.

The identifiers of genomic marker, as well as the identifiers of non-genomic markers, are encrypted through a deterministic encryption scheme, by using a symmetric key SK previously established between the certified institution CI and the user MC. Deterministic encryption, as opposed to probabilistic encryption (e.g., homomorphic encryption), is a particular form of encryption that produces always the same ciphertext for a given plaintext and key. As a result, this type of encryption prevents the Data Center DC from knowing which markers (SNP or phenotypes) are tested during a genetic association study but still allows for equality checks for executing matching queries within the database and for checking user MC's access rights.

In step G, one user MC transmits to the Data Center DC a selection of encrypted identifiers of patient markers which the user MC needs in order to compute some results, for example in order to infer a risk (arrow 105). This selection could be implicit. The selection could include for example a list of identifiers of columns, encrypted with the symmetric key SK. Each encrypted identifier indicates one column in the patient's genomic and non-genomic matrices 400, 401, or 402 which should be used to compute a result, for example to infer a risk to which the patient is exposed. Note that to prevent the DC from learning the nature of the test based on the number of requested markers, the user MC might send a fixed number of markers for each test, including some random dummy markers with null contribution to the computation of a result.

During step H, the patient markers corresponding to the selection of identifiers are retrieved by Data Center DC. This step could be implicit. Those markers are transmitted to the user MC.

During step I, the user MC performs computations in the encrypted domain onto at least some of the patient markers received from the Data Center. The outcome of this step is an encrypted result, such as an encrypted evaluation of a disease susceptibility.

In the case of a risk test, the computation may be performed as follows. Let $SNV_i$ represent the ID of a SNV, $SNV_i^P$ represent the value of $SNV_i$ for patient P, and $[SNV_i^P]$ denote its encryption under the homomorphic scheme. Let also $<SNV_i>$ be the encrypted ID of a SNV using the symmetric key.

In the medical field, the genetic risk score, $\mathbb{G}(X)$, is generally computed with an additive model. The computation of its encrypted version, $[\mathbb{G}(X)]$, is based on the homomorphic properties of the cryptosystem, as shown below:

$$[\mathbb{G}(X)] = \left[\alpha + \sum_{SNP_i \in \varphi} \beta_i SNP_i^P\right] = [\alpha] \times \prod_{SNP_i \in \varphi} [SNP_i^P]^{\beta_i},$$

where $\beta_i$ represents the contribution of $SNV_i$ to condition X and $\alpha$ represents the baseline risk.

In order to allow for the integration of non-genomic factors (such as clinical and/or environmental factors) and ancestry information into the risk computation, markers in tables 401 and 402 are further used in the computation of the risk result. These further components are useful when there are strong known influences of environment or ancestry on a particular trait, such as metabolic disorders, because they increase the accuracy of the test.

Let $[F_i^P]$, where $F_i^P \in \{0, 1\}$, be the encrypted value of a non-genomic factor, and: $\sigma=\{<F_i(X)>\}$ be the collection of the encrypted non-genomic factors' identifiers that are required for the computation of the risk for condition X. Let also $[A_i^P]$ where $A_i^P \in \{0, 1\}$, be the encrypted value of an ancestry group and $<A_i(X)>$ be the ancestry group relevant for testing on condition X. Then, similarly to the previous additive model, the overall encrypted risk result $[S(X)]$ (which includes genomic, non-genomic and ancestry information) is computed as follows:

$$[\mathbb{S}(X)] = \left[A_i^P \times \left(\mathbb{G}(X) + \sum_{F_i \in \vartheta} w_i F_i^P\right)\right] =$$

$$= [A_i^P] \circ \left([\mathbb{G}(X)] \times \prod_{F_i \in \vartheta} [F_i^P]^{w_i}\right),$$

where ωi represents the contribution of i-th non-genomic factor to condition X and $\circ$ represents a secure two-party multiplication protocol. During step J, the user MC transmits this encrypted result to the Data Center DC (arrow 105), which partly decrypts it with its part $prk_i^2$ of the private key, thus obtaining a partly decrypted test result. "Partly decrypted" means in this context that a known asymmetrical decryption function is applied to the encrypted result, using the second part $prk_i^2$ of the private key as parameter. However, since only a part of the private key is used for the decryption, the outcome of this step is still ciphered and meaningless for the DC.

In step K, the partly decrypted result is transmitted to the user MC (arrow 106), which then decrypts it with its first part $prk_i^1$ of the private key, thus obtaining a decrypted test result during step L, without revealing to the user any unencrypted patient markers.

In another embodiment (not shown), the computation of the result is performed by the data Center DC, and partly decrypted in the Data Center with the second part of the private key before being sent to the user MC which makes the final decryption with its first part of the private key. However, this is less secure since the Data Center may determine which test is performed for the user (without however accessing to the test result).

FIG. 4 illustrates an example of representation of the patient's encrypted genomic and clinical and/or environmental markers (data). In this example, this data is represented in three tables or matrices, one (400) containing the encrypted genotype markers ($\mathbb{G}$), such as the single-nucleotide polymorphisms (SNPs), another one (401) containing the non-genetic information ($\mathbb{P}$), and the last one (402) the ancestry markers [$\mathbb{A}$]. Each row of $\mathbb{G}$ contains the set of encoded and encrypted SNP genotypes for a single participant while each column corresponds to a SNP's identifier. Each element $G_i^j$ of the table contains the i-th patient's genotype for the j-th SNP.

The ancestry markers stored in table [$\mathbb{A}$] for a particular patient only need to be inferred once for each patient, and could then be reused for different tests for this patient, or to compute future results for this patient.

The encrypted ancestry markers in table 402 can be accurately inferred by applying principal components analysis (PCA) to genotype data from an admixed population. Intuitively, PCA infers continuous axes (or principal components) of genetic variation; these axes reduce the data to a small number of dimensions, and describe as much variability as possible. In data sets with ancestry differences between samples, these axes often have a geographical interpretation. For example, in the clustered chart 709 of FIG. 5, by accurately identifying European (600), African (601) and Asian (602) groups, the top two axes PC1, PC2 of variation well reflect the structure in continental populations. It is thus possible to infer a patient's ancestry groups from his genotype data.

In one embodiment, the ancestry markers are inferred by the certified institution CI or by the key manager, based on the SNPs of this patient. They are then anonymized, encoded, encrypted and sent as table [$\mathbb{A}$] to the Data Center DC (arrow 104).

Figure 6:
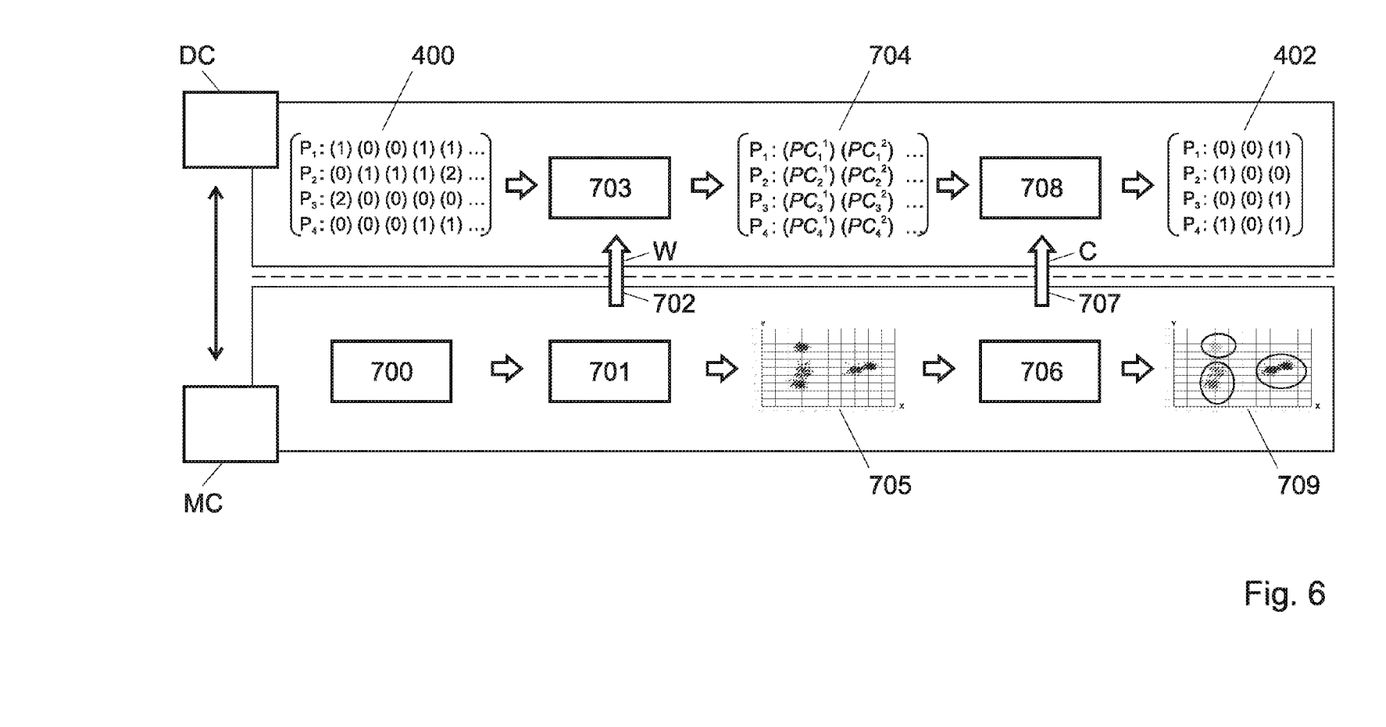
FIG. 6 schematically illustrates how ancestry groups are inferred.

In another embodiment, illustrated on FIG. 6, the ancestry markers are inferred during a secure two-party protocol that takes place between the user MC and Data Center DC during an initial pre-processing phase, or during the same process also used for inferring other test results.

In the initial step of the privacy-preserving ancestry-inference method illustrated on FIG. 6, a principal components analysis is performed by the user MC, or by any other entity, on an external reference panel (or training set) 700 of plaintext genotypes. As a result of such a PCA, a set of SNP weights is obtained that will then be used to predict the encrypted principal components (PCs) for each patient. The ancestry information can then be extracted from the encrypted PCs of each patient.

In a first step of FIG. 6, an external reference panel 700 is selected, for example by the user MC. The reference panel 700 consists of genotype samples from an admixed population that share a similar structure with the patient's population. Such a panel can be retrieved from international genomics-related projects like the HapMap project or the 1000 Genomes project, where admixed populations have been extensively studied.

Then, at step 701 of FIG. 6, the external reference panel 700 is used as a training set for the principal components analysis PCA, resulting in an unclustured chart 705.

Let $\mathbb{X}$ be the V×N matrix of encoded SNPs for the reference panel composed of N individuals with V SNPs. Then, by performing a PCA on $\mathbb{X}^T\mathbb{X}$, the user MC obtains an N×N matrix $\mathbb{U}$ and a N×N diagonal matrix $\mathbb{S}$. $\mathbb{U}$ represents the set of orthonormal eigenvectors or principal components (PCs) for the symmetric matrix $\mathbb{X}^T\mathbb{X}$ and $\mathbb{S}$ is the matrix with the k-th largest eigenvalue at the k-th diagonal element. The SNP weights are computed as $\mathbb{W} = \mathbb{S}^{-1}(\mathbb{X}\mathbb{U})^T$. Note that W is a N×V matrix with the SNP weights for predicting the k-th PC in the k-th row.

During step 706 of FIG. 6, a cluster analysis is performed by the user MC or by any other entity to automatically identify the main ancestry groups within the reference panel population.

Figure 5:
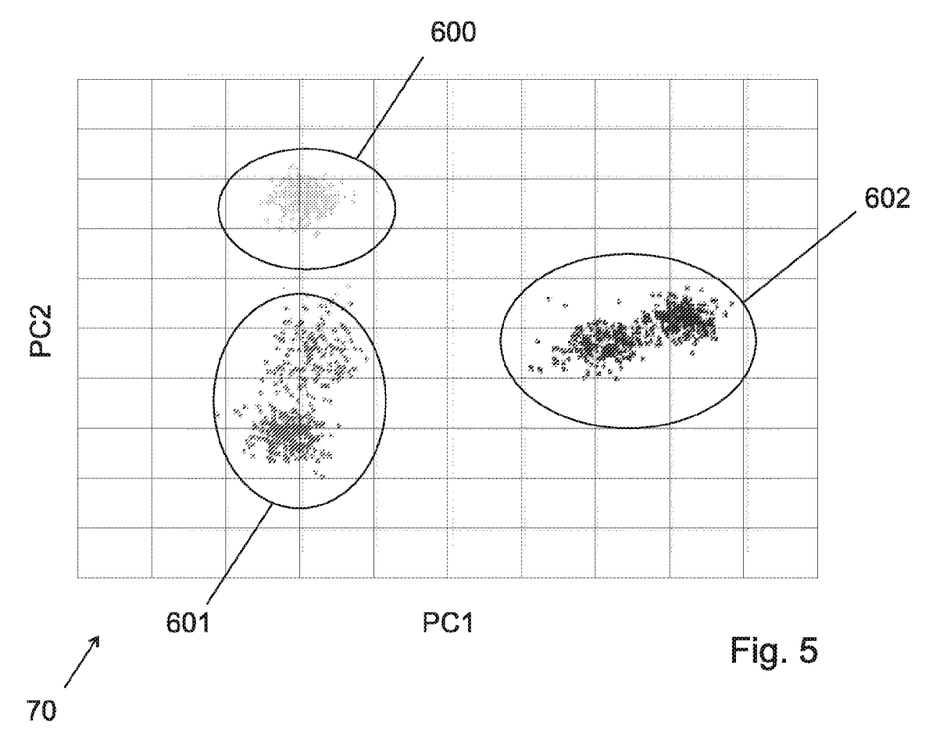
FIG. 5 illustrates two principal components that could be used for identifying European, African and Asian groups.

Let $\mathbb{W}_L$ be the matrix obtained by keeping only the first L principal components of $\mathbb{W}$ that best describe patient's population structure. Once the matrix $\mathbb{W}_L$ is computed by keeping the SNP weights for the L top principal components, the user MC (for example) computes an N×L matrix $\mathbb{X}_L$ ($\mathbb{W}_L \times \mathbb{X}$). The matrix $\mathbb{X}_L$ contains the principal components PCs for each individual in the reference panel. Note that in this way the reference panel is reduced to L dimensions. Then, the user MC performs a K-means clustering on the $\mathbb{X}_L$ matrix in order to partition the N individuals of the reference panel into K clusters or ancestry groups, as indicated on clustered Chart 709. Each individual belongs to the ancestry group with the nearest mean, that serves as an identifier of the ancestry group itself. Finally, the user MC or clustering entity sends a vector $\mathbb{C}$ (arrow 707), which contains the means of the clusters, to the Data Center DC to compare them with the encrypted PCs of each participant and, thus infer his ancestry group.

Then, after selecting the L top principal components PCs, the user MC sends the SNP weights $\mathbb{W}_L$ to the DC along with the encrypted identifiers of the SNPs in the reference panel (arrow 702). L=2 has been proved to be a reasonable value for identifying continental ancestry groups in admixed populations, but a higher number of principal components could also be used.

In step 703 of FIG. 6, the DC (or the user MC) computes the encrypted top L principal components PCs for each patient by applying the SNPs weights $\mathbb{W}_L$ to their encoded and encrypted SNPs 400 through homomorphic computations.

Therefore, once the SNP weights and the SNP identifiers are received, the Data Center DC (or the user MC) selects, from [ $\mathbb{G}$ ], the columns corresponding to the V SNPs which needs to be used in order to compute $\mathbb{W}_L$. Let I be the total number of participants and [ $\mathbb{G}$ ] be the I×V submatrix extracted from [s], then the encrypted principal components are computed as [PC]=[ $\mathbb{G}$ $\mathbb{W}^T$ ]

In particular, each element $[PC_i^l]$ of the I×L matrix [ $\mathbb{P}\mathbb{C}$ ] (704) is computed through homomorphic operations as follows:

$$[PC_i^l] = \left[\sum_{v=1}^{V} G_i^v \cdot W_v^l\right] = \prod_{v=1}^{V} [G_i^v]^{w_v^l}.$$

During step 708 of FIG. 6, and given the encrypted principal components [ $\mathbb{P}\mathbb{C}$ ] of the participants and the plaintext vector of cluster means $\mathbb{C}$, the Data Center DC infers the encrypted ancestry group of each participant through a secure similarity protocol. Intuitively, without revealing any sensitive information, the DC assigns each participant to one of the K ancestry groups based on the maximum similarity between his encrypted PCs and the cluster means. In summary, for each participant, the protocol consists in (i) securely computing the similarity between his encrypted PCs and each cluster's mean, (ii) finding the maximum encrypted similarity, and (iii) computing the encrypted binary values that indicate the ancestry group he belongs to.

A possible algorithm for this secure similarity protocol used at step 708 could use the function 1 below. It consists of a secure two-party comparison sub-function that, given two ciphertexts [a] and [b] encrypted under the same public key pbk, outputs the encrypted result of their comparison. Let $$f_C([a];[b])$$

represent the encrypted result of the comparison protocol with inputs [a] and [b], where a and b are l-bit integers. Then, $f_C$([a]; [b]) outputs the encryption of 1 when a∘b and, otherwise, the encryption of 0.

This function could thus be used in order to compare the encrypted principal components 703 for a particular patient P with the cluster means C retrieved from the reference panel 700. Note that homomorphic encryption does not preserve any order in the ciphertext domain, hence Algorithm 1 allows the MC and the DC to compare two ciphertexts in a privacy-preserving way.

---

Algorithm 1 Secure Comparison $f_c$([a], [b])

---

Input: @DC: [a], [b] and $prk^1$. @MC: $prk^2$.
Output: @DC: $f_c$([a], [b]) = [(a ≤ b)]. @MC: ⊥.
 //Let a and b be two l-bit integers
1: DC computes [z] ← [a] * $[b]^{-1}$ * $[2^l]$ = [a − b + $2^l$].
2: DC generates a random number r,0 ≤ r < $n^2$, and blinds
    [z]: [ẑ] ← [z] * [r] = [z + r].
3: DC partially decrypts [ẑ], (ẑ) ← D((ẑ), $prk^1$), and sends (ẑ) to MC.
4: MC decrypts (ẑ) with $prk^2$, ẑ ← D((ẑ), $prk^2$)
5: MC computes β ← ẑ mod $2^l$
6: DC computes α ← r mod $2^l$.
7: DC and MC run a DGK or a modified DGK comparison with private
    inputs α and β and obtain $δ_{DC}$ (@DC) and $δ_{MC}$ (@DC).
8: MC computes $\left[\frac{ẑ}{2^l}\right]$ and sends $\left[\frac{ẑ}{2^l}\right]$ and $[δ_{MC}]$ to DC.
9: DC computes [(β < α)]:
    if $δ_{DC}$ = 1 then [(β < α)] ← $[δ_{MC}]$,
    else [(β < α)] ← [1] * $[δ_{MC}]^{-1}$.
10: DC computes
    $$[(a \le b)] \leftarrow \left[\frac{ẑ}{2^l}\right] * \left(\left[\frac{r}{2^l}\right] * [(\beta < \alpha)]\right)^{-1}$$

---

The DGK comparison is optimized for the secure comparison of integer; it is more efficient than Paillier cryptosystems in terms of encryption and decryption due to its smaller message space. The modified DGK comparison, as described in T. Veugen, "Improving the DGK comparison protocol", in 2012 IEEE International Workshop on Information Forensics and Security (WIFS), 2012, pp. 49-54, could be used in the above mentioned function in order to achieve perfect security for both parties involved in a protocol, with only a small increase in communication and computational complexity.

In one embodiment, the method of the invention further uses a secure two-party multiplication protocol that, given two ciphertexts [a] and [b] encrypted under the same public key, provides the encryption of their corresponding plaintexts. Note that the modified Paillier cryptosystem used for encryption in step E of the method is only additively homomorphic and does not support multiplication between ciphertexts. Therefore, a two-party function should be used that, given two ciphertexts encrypted by an additively homomorphic scheme, allows to compute the encryption of the multiplication of the two corresponding plaintexts. Let the user MC and the DC participate in the secure multiplication protocol. We assume that the user MC has two encrypted values, [a] and [b], and one private share $prk_1$, and that the DC has the other private share $prk_2$. Then, the protocol outputs [a×b] to the user MC without revealing a and b to the DC. The following algorithm could be used for this multiplication:

---

Algorithm 2 Secure Multiplication [a] ⊗ [b] = [a × b]

---

Input: @DC [a], [b] and $prk^2$. @MC: $prk^1$.
Output: @DC: [a * b]. @MC: ⊥.
1: DC generates two random numbers $r_1$ and $r_2$.
2: DC randomizes [a] and [b] by homomorphically subtracting the two
    random numbers numbers $r_1$ and $r_2$:
    [â] ← [a] * $[-r_1]$ = [a − $r_1$],
    [b̂] ← [b] * $[-r_2]$ = [b − $r_2$].
3: DC partially decrypts [â] and [b̂] with $prk^2$:
    ⟨â⟩ ← D([â], $prk^2$),
    ⟨b̂⟩ ← D([b̂], $prk^2$).
4: DC sends ⟨â⟩ and ⟨b̂⟩ to MC.
5: MC decrypts ⟨â⟩ and ⟨â⟩ with $prk^1$
    â ← D(⟨â⟩, $prk^1$),
    b̂ ← D(⟨b̂⟩, $prk^1$).
6: MC computes [â * b̂] and sends it to DC.

-continued

Algorithm 2 Secure Multiplication [a] ⊗ [b] = [a × b]

7: DC computes the encrypted product between a and b
$[a * b] \leftarrow [\hat{a} * \hat{b}] * [a]_2^{r} * [b]_2^{r} * [-r_1 * r_2] =$
$[\hat{a} * \hat{b} + r_2 * b - r_1 + r_2].$ The secure similarity step 708 requires as input parameters the matrix of encrypted principal components [ℙℂ] along with the vector of clusters' means ℂ; it outputs the encrypted matrix 402 of ancestry information [𝔸]. The details of the protocol are described in Algorithm 3:

Algorithm 3 Secure Similarity Protocol

Input: @DC[PC] and C. @MC: ⊥,
Output: @DC: [Λ]. @MC: ⊥
//
Let I be number of participants, K number of ancestry groups (or clusters),
and L number of selected top PCs.
1: for all i : 0 < i ≤ I do
// DC computes the encrypted similarities between encrypted PCs and cluster means:
2: for all k : 0 < k ≤ K do
3: $[Sim_j^k] \leftarrow \Sigma_{l=1}^{L} [PC_j^l * C_l^k] = \Pi_{l=1}^{L} [PC_j^l]^{c_l^k}.$
4: end for
//DC computes the maximum similarity:
5: $[M_1] \leftarrow [Sim_j^{l}].$
6: for all k : 1 < k ≤ K do
7: $[M_1] \leftarrow [M_1 * (Sim_j^k \leq M_1) + Sim_i^k * (M_1 \leq Sim_j^k)] = \{[M_1] \otimes f_c ([M_1], [Sim_j^k])\}$
8: end for
// DC computes the encrypted value of each ancestry group for each participant:
9: for all k : 0 < k ≤ K do
10: $[A_j^k] \leftarrow f_c ([M_1], [Sim_j^k])$
11: end for
12: end for Once [𝔸] is obtained, this can be used in step I of the online phase, during which the user MC and the Data Center DC collaborate for the privacy-preserving computation of a risk test. The user obtains only the final result of the computation without seeing the plaintext genomes of the patients.

The above mentioned steps A to L might be executed in alphabetical order or, when suitable, in any other order.

The invention is also related to a computer readable storage medium having recorded thereon a computer program for performing a disease susceptibility test on a patient, said test comprising:

(I) performing homomorphic computations, so as to retrieve an encrypted test result;

(J) partly decrypting said test result with a first part of a private key, (L) sending the partly decrypted result to a user, wherein said homomorphic computations are based on encrypted genomic markers of the patient, on encrypted clinical and/or environmental markers, and on encrypted ancestry markers of the patient.

The invention is further related to a computer readable storage medium having recorded thereon a computer program for performing a disease susceptibility test on a patient, said test comprising:

transmitting to a data center a selection of identifiers of patient markers, at least some of said identifiers identifying genomic markers, on clinical and/or environmental markers, and ancestry markers of the patient;

receiving from said data center a partly decrypted result of an homomorphic computation based on identified encrypted genomic markers of the patient, on identified encrypted clinical and/or environmental markers, and on identified encrypted ancestry markers of the patient;

decrypting the partly decrypted result with a second part of said private key.

The invention claimed is:

1. A privacy-preserving method for performing a disease susceptibility test on a patient, said method comprising:
    (A) generating a pair of encryption keys comprising a private key and a public key corresponding to said private key;
    (B) dividing said private key in a first part and in a second part;
    (C) transmitting the first part to one user of an encrypted test result over a data network or through a shared store, and transmitting the second part to a data center over a data network or through a shared store, said data center being a processing unit that performs computation and storage tasks;
    (I) performing homomorphic computations with a computation module, so as to retrieve the encrypted test result to evaluate a disease susceptibility;
    (J) partly decrypting said test result with the first part of the private key,
    (L) decrypting the partly decrypted result with the second part of said private key, using a cryptographic module;
    wherein said homomorphic computations are based on encrypted genomic markers of the patient, on encrypted clinical and/or environmental markers, and on encrypted ancestry markers of the patient.

2. The method of claim 1, further comprising:
    (D) retrieving a set of patient markers including said genomic markers and said clinical and environmental markers;
    (E) individually encrypting a plurality of said patient markers with said public key;
    (F) making at least some of said encrypted patient markers available to said data center.

3. The method of claim 2, wherein said homomorphic computations are performed by said user,
    said step (J) of obtaining the test result which is partly decrypted being performed at said data center,
    said step (L) of decrypting said partly decrypted result being performed by said user.

4. The method of claim 2, wherein said homomorphic computations are performed in said data center,
    said step (J) of obtaining the test e-result which is partly decrypted being performed at said data center,
    said step (L) of decrypting said partly decrypted result being performed by said user.

5. The method of claim 2, said user being a medical clinic.

6. The method of claim 2, said user being a device such as a personal computer, tablet, mobile phone, laptop or smart card.

7. The method of claim 1, further comprising:
    (G) transmitting to said data center a selection of identifiers of patient markers, at least some of said patient markers being required for said homomorphic computation;
    (H) retrieving in said data center patient markers corresponding to said selection of identifiers.

8. The method of claim 7, wherein said selection of identifiers are encrypted with a symmetric key known by said user and unknown by said data center, so as to prevent said data center from knowing which patient markers are tested.

9. The method of claim 7, wherein said selection of identifiers comprises dummy identifiers for markers with no contribution to said test result, in order to conceal the type of said test result from said data center.

10. The method of claim 1, wherein said encrypted ancestry markers are inferred from genomic markers or from said encrypted genomic markers of the patient.

11. The method of claim 10, further comprising
transmitting weights to said data center,
said step (I) of performing homomorphic computations further comprising using said weights and said encrypted genomic markers for inferring an encrypted ancestry group with a principal component analysis.

12. The method of claim 10, said step of inferring the ancestry markers comprising a determination of the similarity between said genomic markers and a plurality of clusters, each cluster corresponding to one ancestry group.

13. The method of claim 12, said determination of similarity being performed in an encrypted domain.

14. The method of claim 10, further comprising a step of performing a Principal Component Analysis on an external reference panel of genotypes, and a step of clustering the results of said Principal Component Analysis.

15. A data center, comprising:
a storage module for storing a set of encrypted patient markers including genomic markers, clinical and environmental markers, and ancestry markers;
a module for transmitting a selection of patient markers to a user;
a module for receiving an encrypted result from said user;
a cryptographic module arranged for decrypting said encrypted test result with a part of a private key;
means for transmitting the partly decrypted result to said user (MC),
wherein said data center is a processing unit that performs computation and storage tasks.

16. A data center, comprising:
a storage module for storing a set of patient markers including genomic markers, clinical and environmental markers, and ancestry markers;
a computing module arranged for performing homomorphic computations based on said genomic markers, on said clinical and environmental markers, and on said ancestry markers, so as to retrieve an encrypted result;
a cryptographic module arranged for decrypting said encrypted test result with a part of a private key;
means for transmitting the partly decrypted result to one user,
wherein said data center is a processing unit that performs computation and storage tasks.

17. The data center of claim 16, said computing module being arranged for determining a similarity between some genomic markers and a plurality of clusters, so as to retrieve encrypted ancestry markers.

18. A user system comprising:
means for transmitting to a data center identifiers of patient genomic, clinical and environmental, and ancestry markers;
means for receiving encrypted genomic, clinical and environmental, and ancestry markers;
computations based on said genomic markers, on said clinical and environmental markers, and on said ancestry markers, so as to retrieve an encrypted result;
means for transmitting the encrypted result to said data center;
means for receiving a partly decrypted result;
a cryptographic module arranged for decrypting said partly decrypted result with a part of a private key.

19. A computer readable storage medium having recorded thereon a computer program for performing a disease susceptibility test on a patient, said test comprising:
(A) generating a pair of encryption keys comprising a private key and one a public key corresponding to said private key;
(B) dividing said private key in a first and second parts;
(C) making the first part available to one user of an encrypted test result, and the second part available to a data center;
(I) performing homomorphic computations, so as to retrieve an encrypted test result to evaluate a disease susceptibility;
(J) partly decrypting said test result with a first part of a private key,
(L) sending the partly decrypted result to a user,
wherein said homomorphic computations are based on encrypted genomic markers of the patient, on encrypted clinical and/or environmental markers, and on encrypted ancestry markers of the patient, wherein the computer readable storage medium comprises at least one non transitory storage medium.

20. A computer readable storage medium having recorded thereon a computer program for performing a disease susceptibility test on a patient, said test comprising:
transmitting to a data center a selection of identifiers of patient markers, at least some of said identifiers identifying genomic markers, on clinical and/or environmental markers, and ancestry markers of the patient;
receiving from said data center a partly decrypted result of an homomorphic computation based on identified encrypted genomic markers of the patient, on identified encrypted clinical and/or environmental markers, and on identified encrypted ancestry markers of the patient;
decrypting the partly decrypted result with a second part of a private key,
wherein the computer readable storage medium comprises at least one non transitory storage medium.

* * * * *